(12) United States Patent
Howard et al.

(10) Patent No.: US 10,596,372 B2
(45) Date of Patent: Mar. 24, 2020

(54) TARGETED STEERABLE TRANSCRANIAL INTERVENTION TO ACCELERATE MEMORY CONSOLIDATION

(71) Applicant: HRL Laboratories, LLC, Malibu, CA (US)

(72) Inventors: Michael D. Howard, Westlake Village, CA (US); Praveen K. Pilly, West Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 11 days.

(21) Appl. No.: 15/990,460

(22) Filed: May 25, 2018

(65) Prior Publication Data

US 2018/0272129 A1 Sep. 27, 2018

Related U.S. Application Data

(63) Continuation-in-part of application No. 15/947,733, filed on Apr. 6, 2018, now Pat. No. 10,413,724, (Continued)

(51) Int. Cl.
*A61N 1/36* (2006.01)
*A61N 1/02* (2006.01)
*A61N 1/04* (2006.01)

(52) U.S. Cl.
CPC ......... *A61N 1/36025* (2013.01); *A61N 1/025* (2013.01); *A61N 1/0456* (2013.01);
(Continued)

(58) Field of Classification Search
CPC .............. A61N 1/36025; A61N 1/0476; A61N 1/36031; A61N 1/0484; A61N 1/0456; A61N 1/025; A61N 1/36034
See application file for complete search history.

(56) References Cited

U.S. PATENT DOCUMENTS 6,435,876 B1 8/2002 Chen
6,751,505 B1 6/2004 Van Den Honert
(Continued)

FOREIGN PATENT DOCUMENTS

EP 2409641 A1 1/2012
JP 2005-173081 A 6/2005
(Continued)

OTHER PUBLICATIONS

Nir Grossman, et al., (2017). Noninvasive Deep Brain Stimulation via Temporally Interfering Electric Fields. Cell 169, pp. 1029-1041 Jun. 1, 2017. Elsevier Inc. http://dx.doi.org/10.1016/j.cell.2017.05.024.

(Continued)

*Primary Examiner* — Rex R Holmes
(74) *Attorney, Agent, or Firm* — Tope-McKay & Associates

(57) ABSTRACT

Described is a system to accelerate memory consolidation using a steerable transcranial intervention. During operation, the system generates a unique transcranial and steerable stimulation tag to associate with memory of a task or event. Once the tag is generated, the system activates a plurality of electrodes (e.g., as few as four) to apply the unique transcranial stimulation tag during the occurrence of the event or task to be consolidated.

21 Claims, 8 Drawing Sheets

Related U.S. Application Data which is a continuation-in-part of application No. 15/583,983, filed on May 1, 2017, now abandoned, which is a continuation-in-part of application No. 15/332,787, filed on Oct. 24, 2016, now Pat. No. 10,307,592, said application No. 15/947,733 is a continuation-in-part of application No. 15/332,787, filed on Oct. 24, 2016, now Pat. No. 10,307,592, which is a continuation-in-part of application No. 15/227,922, filed on Aug. 3, 2016, now Pat. No. 10,092,753.

(60) Provisional application No. 62/570,669, filed on Oct. 11, 2017, provisional application No. 62/558,133, filed on Sep. 13, 2017, provisional application No. 62/537,892, filed on Jul. 27, 2017, provisional application No. 62/516,350, filed on Jun. 7, 2017, provisional application No. 62/330,440, filed on May 2, 2016, provisional application No. 62/247,435, filed on Oct. 28, 2015, provisional application No. 62/245,730, filed on Oct. 23, 2015, provisional application No. 62/210,890, filed on Aug. 27, 2015, provisional application No. 62/210,907, filed on Aug. 27, 2015.

(52) U.S. Cl.
CPC ......... *A61N 1/0476* (2013.01); *A61N 1/0484* (2013.01); *A61N 1/36031* (2017.08); *A61N 1/36034* (2017.08)

(56) References Cited

U.S. PATENT DOCUMENTS

| | | | |
|---|---|---|---|
| 7,153,139 | B2 | 12/2006 | Wen et al. |
| 8,718,778 | B2 | 5/2014 | Bikson et al. |
| 9,116,835 | B1 | 8/2015 | Smyth |
| 9,149,599 | B2 | 10/2015 | Walter |
| 9,370,658 | B2 | 6/2016 | Neuvonen |
| 2003/0225340 | A1 | 12/2003 | Collura |
| 2006/0041242 | A1 | 2/2006 | Stypulkowski |
| 2007/0060974 | A1 | 3/2007 | Lozano |
| 2007/0213786 | A1 | 9/2007 | Sackellares et al. |
| 2009/0112278 | A1* | 4/2009 | Wingeier ............ A61B 5/6864 607/45 |
| 2009/0319002 | A1 | 12/2009 | Simon |
| 2011/0015469 | A1* | 1/2011 | Walter ............ A61M 21/02 600/27 |
| 2011/0118534 | A1 | 5/2011 | Baror |
| 2011/0159467 | A1 | 6/2011 | Peot |
| 2011/0288610 | A1 | 11/2011 | Brocke |
| 2012/0046531 | A1 | 2/2012 | Hua |
| 2012/0184870 | A1 | 7/2012 | Shaw |
| 2012/0245653 | A1 | 9/2012 | Bikson et al. |
| 2012/0265261 | A1 | 10/2012 | Bikson |
| 2013/0011817 | A1 | 1/2013 | Cohen Kadosh |
| 2013/0225953 | A1 | 8/2013 | Oliviero |
| 2013/0288223 | A1 | 10/2013 | Watterson |
| 2013/0338738 | A1 | 12/2013 | Garcia Molina |
| 2014/0038147 | A1 | 2/2014 | Morrow |
| 2014/0057232 | A1 | 2/2014 | Wetmore et al. |
| 2014/0288614 | A1 | 5/2014 | Hagedorn |
| 2014/0275926 | A1 | 9/2014 | Scott et al. |
| 2015/0025590 | A1 | 1/2015 | Cheng |
| 2015/0050623 | A1 | 2/2015 | Falash |
| 2015/0066104 | A1 | 3/2015 | Wingeier |
| 2015/0079560 | A1 | 3/2015 | Cowan |
| 2015/0105837 | A1 | 4/2015 | Aguilar Domingo |
| 2015/0174418 | A1 | 6/2015 | Tyler |
| 2015/0238762 | A1 | 8/2015 | Pal |
| 2015/0294074 | A1 | 10/2015 | Kawato |
| 2016/0175589 | A1 | 6/2016 | Wingeier |
| 2016/0206871 | A1 | 7/2016 | Weisend |
| 2016/0220850 | A1 | 8/2016 | Tyler |
| 2016/0228702 | A1 | 8/2016 | Kempe |
| 2016/0256691 | A1 | 9/2016 | Cecchi |
| 2017/0014630 | A1 | 1/2017 | Fried et al. |
| 2017/0043167 | A1 | 2/2017 | Widge |
| 2017/0249853 | A1 | 8/2017 | Weiss |
| 2017/0304623 | A1 | 10/2017 | Tandon |
| 2018/0169411 | A1 | 6/2018 | Goodall |
| 2018/0221644 | A1 | 8/2018 | Grill |

FOREIGN PATENT DOCUMENTS

| | | | |
|---|---|---|---|
| WO | WO2016-102602 | A1 | 6/2016 |
| WO | WO 2016-182947 | A1 | 11/2016 |

OTHER PUBLICATIONS

Woods et al. (2016). A technical guide to tDCS, and related non-invasive brain stimulation tools. Clinical Neurophysiology, 127: pp. 1031-1048.

Santostasi, Giovanni, et al. "Phase-locked loop for precisely timed acoustic stimulation during sleep." Journal of neuroscience methods 259 (2016): pp. 101-114.

Liu, Hechen, and Markus Schneider. "Similarity measurement of moving object trajectories." Proceedings of the third ACM SIGSPATIAL international workshop on geostreaming. ACM, 2012, pp. 19-22.

Notification of Transmittal of International Search Report and the Written Opinion of the International Searching Authority for PCT/US2018/034761; dated Sep. 21, 2018.

International Search Report of the International Searching Authority for PCT/US2018/034761; dated Sep. 21, 2018.

Written Opinion of the International Searching Authority for PCT/US2018/034761; dated Sep. 21, 2018.

Nader K, Schafe GE, Le Doux JE. Fear memories require protein synthesis in the amygdala for reconsolidation after retrieval. Nature. 2000; 406: pp. 722-726.

Dudai Y. The neurobiology of consolidations, or, how stable is the engram? Annu. Rev. Psychol. 2004; 55: pp. 51-86.

Squire LR, Alvarez P. Retrograde amnesia and memory consolidation: a neurobiological perspective. Curr. Opin. Neurobiol. 1995; 5: pp. 169-177.

Foa EB. Social anxiety disorder treatments: psychosocial therapies. J. Clin. Psychiatry. 2006; 67 Suppl 12: pp. 27-30.

Seidler GH, Wagner FE. Comparing the efficacy of EMDR and trauma-focused cognitive-behavioral therapy in the treatment of PTSD: a meta-analytic study. Psychol. Med. 2006; 36: pp. 1515-1522.

Bustos SG, Maldonado H, Molina VA. Midazolam disrupts fear memory reconsolidation. Neuroscience. 2006; 139: pp. 831-842.

Sandrini M, Censor N, Mishoe J, Cohen LG. Causal Role of Prefrontal Cortex in Strengthening of Episodic Memories through Reconsolidation. Curr. Biol. 2013; 23: pp. 2181-2184.

Soterix Medical Website. High Definition-transcranial Direct Current Stimulation (HD-tDCS) [Internet]. Available from: http://soterixmedical.com/hd-tdcs, downloaded Aug. 8, 2016, pp. 1-13.

Chan JCK, LaPaglia JA. Impairing existing declarative memory in humans by disrupting reconsolidation. Proc. Natl. Acad. Sci. 2013;110: pp. 9309-9313.

Brunet A, Orr SP, Tremblay J, Robertson K, Nader K, Pitman RK. Effect of post-retrieval propranolol on psychophysiologic responding during subsequent script-driven traumatic imagery in post-traumatic stress disorder. J. Psychiatr. Res. 2008;42: pp. 503-506.

Euston DR, Gruber AJ, McNaughton BL. The role of medial prefrontal cortex in memory and decision making. Neuron. 2012; 76: pp. 1057-1070.

Ji D, Wilson MA. Coordinated memory replay in the visual cortex and hippocampus during sleep. Nat. Neurosci. 2007; 10: pp. 100-107.

Wolters CH, Anwander A, Tricoche X, Weinstein D, Koch MA, MacLeod RS. Influence of tissue conductivity anisotropy on EEG/MEG field and return current computation in a realistic head model:

(56) References Cited

OTHER PUBLICATIONS a simulation and visualization study using high-resolution finite element modeling. NeuroImage. 2006; 30: pp. 813-826.
Dmochowski JP, Datta A, Bikson M, Su Y, Parra LC. Optimized multi-electrode stimulation increases focality and intensity at target. J. Neural Eng. 2011; 8:pp. 046011-1-046011-16.
Edmund Rolls, "The mechanisms for pattern completion and pattern separation in the hippocampus," Front Syst Neurosci. Oct. 2013; vol. 7: Article 74, pp. 1-21.
Thomas J. McHugh, et al., "Dentate Gyrus NMDA Receptors Mediate Rapid Pattern Separation in the Hippocampal Network," Science, vol. 317, (Jul. 2007); pp. 94-99.
Jesse Rissman, et al., "Distributed representations in memory: Insights from functional brain imaging," Annu Rev Psychol. 2012 ; 63: pp. 101-128.
Giulio Ruffinia, et al., "Optimization of multifocal transcranial current stimulation for weighted cortical pattern targeting from realistic modeling of electric fields," Neuroimage. Apr. 1, 2014; 89: pp. 216-225.
Office Action 1 for U.S. Appl. No. 15/072,353, dated Oct. 19, 2016.
Tremblay, Sara, et al., "The uncertain outcome of prefrontal TDCS," Brain Stimulation 7.6 (2014): pp. 773-783. Web.
Segrave, R.A., et al., "concurrent cognitive control training augments the anidepressant efficacy of TDCS: A pilot study," Brain Stimulation 7.2 (2014): pp. 325-331. Web.
Castano-Candamil, Sebastian, et al., "Solving the EEG inverse problem based on space-time-frequency structured sparsity constraints," Neuroimage 118 (2015), pp. 598-612. Web.
Response to Office Action 1 for U.S. Appl. No. 15/072,353, dated Feb. 17, 2017.
Office Action 2 for U.S. Appl. No. 15/072,353, dated Apr. 24, 2017.
"An automated pipeline for constructing personalized virtual brains from multimodal neuroimaging data," NeuroImage, vol. 117, Aug. 15, 2015, pp. 343-357.
Krause, M. R., Zanos, T. P., Csorba, B. A., Pilly, P. K., Choe, J., Phillips, M. E., Datta, A., and Pack, C. C. (2017). Transcranial direct current stimulation facilitates associative learning and alters functional connectivity in the primate brain. Current Biology, 27(3), pp. 3086-3096.
Response to Office Action 2 for U.S. Appl. No. 15/072,353, dated Aug. 22, 2017.
Office Action 3 for U.S. Appl. No. 15/072,353, dated Oct. 6, 2017.
Response to Office Action 3 for U.S. Appl. No. 15/072,353, daetd Jan. 8, 2018.
Notice of Allowance for U.S. Appl. No. 15/072,353, dated Apr. 17, 2018.
McNamara CG, Tejero-Cantero A, Trouche S, Campo-Urriza N, Dupret D. Dopaminergic neurons promote hippocampal reactivation and spatial memory persistence. Nat Neurosci. 2014;17: pp. 1658-1660.
Marshall L, Helgadóttir H, Mölle M, Born J. Boosting slow oscillations during sleep potentiates memory. Nature. 2006;444: pp. 610-613.
Javadi AH, Walsh V. Transcranial direct current stimulation (tDCS) of the left dorsolateral prefrontal cortex modulates declarative memory. Brain Stimulat. 2012;5: pp. 231-241.
Rasch B, Rüchel C, Gais S, Born J. Odor cues during slow-wave sleep prompt declarative memory consolidation. Science. 2007;315: pp. 1426-1429.
Rudoy JD, Voss JL, Westerberg CE, Paller KA. Strengthening Individual Memories by Reactivating Them During Sleep. Science. 2009;326: p. 1079.
Bendor D, Wilson MA Biasing the content of hippocampal replay during sleep. Nat. Neurosci. 2012;15: pp. 1439-1444.
Abeyratne UR, Swarnkar V, Rathnayake SI, Hukins C. Sleep-stage and event dependency of brain asynchrony as manifested through surface EEG. Conf. Proc. Annu. Int. Conf. IEEE Eng. Med. Biol. Soc. IEEE Eng. Med. Biol. Soc. Conf. 2007;2007: pp. 709-712.
Salmi T, Brander PE. Computer assisted detection of REM and non-REM sleep for analysis of nocturnal hypoxaemia in patients with ventilatory impairment. Int. J. Clin. Monit. Comput. 1994;11: pp. 63-70.
Euston et al. Fast-Forward Playback of Recent Memory Sequences in Prefrontal Cortex During Sleep. Science. Nov. 2007; 318 (5853): pp. 1147-1150.
The SenseWear armband as a Sleep Detection Device [Internet]. [cited Nov. 23, 2014]. pp. 1-9. Available from: http://www.bodymedia.com/Professionals/Whitepapers/The-SenseWear-armband-as-a-Sleep-Detection-Device?whence=.
Ruffini et al., Optimization of multifocal transcranial current stimulation for weighted cortical pattern targeting from realistic modeling of electric fields, Neuroimage, 89:216-25, 2014.
Rissman and Wagner, "Distributed Representations in Memory: Insights from Functional Brain Imaging," Annual Rev Psychol, 63: 101-128, 2012.
Rolls, "The Mechanisms for Pattern Completion and Pattern Separation in the Hippocampus," Frontiers in Systems Neuroscience, 7: 74, 2013.
McHugh et al, "Dentate Gyrus NMDA Receptors Mediate Rapid Pattern Separation in the Hippocampal Network," Science, 317(5834): 94-99, 2007.
Michael Schirner, et al., "An automated pipeline for constructing personalized virtual brains from multimodal neuroimaging data," NeuroImage, vol. 117, Aug. 15, 2015, pp. 343-357.
Office Action 1 for U.S. Appl. No. 15/227,922, dated Dec. 13, 2016.
Tremblay, Sara, et al. "The Uncertain Outcome of Prefrontal TDCS." Brain Stimulation 7.6 (2014): 773-83. Web.
Segrave, R.A. et al. "Concurrent Cognitive Control Training Augments the Antidepressant Efficacy of TDCS: A Pilot Study." Brain Stimulation 7.2 (2014): 325-31. Web.
Castano-Candamil, Ssebastian et al. "Solving the EEG Inverse Problem Based on Space-Time-Frequency Structured Sparsity Constraints." Neuroimage 118 (2015) 598-612. Web.
Marshall, L. "Transcranial Direct Current Stimulation during Sleep Improves Declarative Memory." Journal of Neuroscience 24.44 (2004): 9985-992. Web.
Javadi, Amir Homayoun, and Paul Cheng. "Transcranial Direct Current Stimulation (tDCS) Enhances Reconsolidation of Long-Term Memory." Brain Stimulation 6.4 (2013): 668-74. Web.
Sahlem, Gregory L., et al. "Oscillating Square Wave Transcranial Direct Current Stimulation (tDCS) Delivered During Slow Wave Sleep Does Not Improve Declarative Memory More Than Sham: A Randomized Sham Controlled Crossover Study." Brain Stimulation 8.3 (2015): 528-34. Web.
Barham, Michael P., Peter G. Enticott, Russell Conduit, and Jarrad A.g. Lum. "Transcranial Electrical Stimulation during, Sleep Enhances Declarative (but Not Procedural) Memory Consolidation: Evidence from a Meta-analysis." Neuroscience & Biobehavioral Reviews 63 (2016): 65-77. Web.
Eggert, Torsten, Hans Dorn, Cornelia Sauter, Michael A. Nitsche, Malek Bajbouj, and Heidi Danker-Hopfe. "No Effects of Slow Oscillatory Transcranial Direct Current Stimulation (tDCS) on Sleep-Dependent Memory Consolidation in Healthy Elderly Subjects." Brain Stimulation 6.6 (2013): 938-45. Web.
Westerberg, Carmen E., Susan M. Florczak, Sandra Weintraub, M.-Marsel Mesulam, Lisa Marshall, Phyllis C. Zee, and Ken A. Paller. "Memory Improvement via Slow-oscillatory Stimulation during Sleep in Older Adults." Neurobiology of Aging 36.9 (2015): 2577-586. Web.
Response to Office Action 1 for U.S. Appl. No. 15/227,922, dated Mar. 13, 2017.
Office Action 2 for U.S. Appl. No. 15/227,922, dated Apr. 24, 2017.
Response to Office Action 2 for U.S. Appl. No. 15/227,922, dated Aug. 24, 2017.
Office Action 3 for U.S. Appl. No. 15/227,922, dated Sep. 29, 2017.
Response to Office Action 3 for U.S. Appl. No. 15/227,922, dated Jan. 29, 2018.
Notice of Allowance for U.S. Appl. No. 15/227,922, dated May 30, 2018.
Grech, R., Cassar, T., Muscat, J., Camilleri, K.P., Fabri, S.G., Zervakis, M., Xanthopoulos, P., Sakkalis, V. and Vanrumste, B.,

(56) References Cited

OTHER PUBLICATIONS

2008. Review on solving the inverse problem in EEG source analysis. Journal of neuroengineering and rehabilitation, 5(1), pp. 1-33.
Tucker DM. Spatial sampling of head electrical fields: the geodesic sensor net. Electroencephalogr. Clin. Neurophysiol, 87: pp. 154-163, 1993.
Michel C., Murray MM. Towards the utilization of EEG as a brain imaging tool, NeuroImage 61 (2012), pp. 371-385.
Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage, 30: pp. 813-826, 2006.
Dmochowski JP, Datta A, Bikson M, Su Y, Parra LC. Optimized multi-electrode stimulation increases focality and intensity at target. J. Neural Eng., 8:046011, 2011, pp. 1-16.
Jones DK and Leemans A, "Diffusion Tensor Imaging", Methods in Molecular Biology 711: pp. 127-144, 2011.
Ramirez, Rey R., and Scott Makeig. "Neuroelectromagnetic source imaging of spatiotemporal brain dynamical patterns using frequency-domain independent vector analysis (IVA) and geodesic sparse Bayesian learning (gSBL)." In Proceedings of the 13th Annual Meeting of the Organization for Human Brain Mapping, Chicago, IL. 2007.
Office Action 1 for U.S. Appl. No. 15/338,118, dated May 23, 2018.
Fox, Peter T., et al., "Column-Based Model of Electric Field Excitation of Cerebral Cortex," Human Brain Mapping 22:1-16 (2004).
Response to Office Action 1 for U.S. Appl. No. 15/338,118, dated Aug. 23, 2018.
Office Action 2 for U.S. Appl. No. 15/338,118, dated Nov. 21, 2018.
Response to Office Action 2 for U.S. Appl. No. 15/338,118, dated Feb. 21, 2019.
Merzagora, Anna C., G. Foffani, I. Panyavin, L. Mordillo-Mateos, J. Aguilar, Banu Onaral, and A. Oliviero. "Prefrontal hemodynamic changes produced by anodal direct current stimulation." Neuroimage 49, No. 3 (2010): pp. 2304-2310.
Christoff, J. A. (2002). Foreign Languages: Human Capital Approach Needed to Correct Staffing and Proficiency Shortfalls. Report to Congressional Requesters, pp. 1-50.
Operation and Maintenance Overview, Fiscal Year 2016 Budget Estimates, Feb. 2015, Office of the Under Secretary of Defense (Comptroller) / Chief Financial Officer, p. 13.
Flöel, A., Rösser, N., Michka, O., Knecht, S., & Breitenstein, C. (2008). Noninvasive brain stimulation improves language learning. Journal of Cognitive Neuroscience, 20(8), pp. 1415-1422.
Fregni, F., Boggio, P. S., Nitsche, M., Bermpohl, F., Antal, A., Feredoes, E., . . . & Pascual-Leone, A. (2005). Anodal transcranial direct current stimulation of prefrontal cortex enhances working memory. Experimental brain research, 166(1), pp. 23-30.
Acheson, D. J., Hamidi, M., Binder, J. R., & Postle, B. R. (2011). A common neural substrate for language production and verbal working memory. Journal of Cognitive Neuroscience, 23(6), pp. 1358-1367.
Anderson, J. R. (1981). Cognitive skills and their acquisition. Psychology Press. pp. 143-146 and pp. 243-249.
Bates, E., & MacWhinney, B. (1989). Functionalism and the competition model. The crosslinguistic study of sentence processing, 3, pp. 73-112.
Hakansson, G. (2005). An introduction to processability theory. Cross-linguistic aspects of processability theory, 30, pp. 179-199.
Schumann, J. H. (1986). Research on the acculturation model for second language acquisition. Journal of multilingual & multicultural development, 7(5), pp. 379-392.
Office Action 1 for U.S. Appl. No. 15/583,983, dated Feb. 12, 2019.
Apoorvagiri; Mental Stress and its Implications on Reaction time; International Journal of Computer Trends and Technology; May 2013; Mental Stress and its Imprilcations on Reaction time. (Year 2013).
Marshall L, Helgadóttir H, Wile M, Born J. Boosting slow oscillations during sleep potentiates memory. Nature. 2006; 444(7119): pp. 610-613.
Rudoy JD, Voss JL, Westerberg CE, Paller KA. Strengthening Individual Memories by Reactivating Them During Sleep. Science. Nov. 20, 2009;326(5956): pp. 1079-1079.
Diekelmann S, Biggel S, Rasch B, Born J. Offline consolidation of memory varies with time in slow wave sleep and can be accelerated by cuing memory reactivations. Neurobiol Learn Mem. Sep. 2012; 98(2): pp. 103-111.
Rasch BH, Born J, Gais S. Combined blockade of cholinergic receptors shifts the brain from stimulus encoding to memory consolidation. J Cogn Neurosci. May 2006; 18(5): pp. 793-802.
Gais S, Born J. Low acetylcholine during slow-wave sleep is critical for declarative memory consolidation. Proc Natl Acad Sci U S A. Feb. 17, 2004; 101(7): pp. 2140-2144.
Rasch B, Buchel C, Gais S, Born J. Odor cues during slow-wave sleep prompt declarative memory consolidation. Science. 2007; 315(5817): pp. 1426-1429.
Kirov R, Weiss C, Siebner HR, Born J, Marshall L. Slow oscillation electrical brain stimulation during waking promotes EEG theta activity and memory encoding. Proc. Natl. Acad. Sci. 2009;106: pp. 15460-15465.
Jutras MJ, Fries P, Buffalo EA. Oscillatory activity in the monkey hippocampus during visual exploration and memory formation. Proc Natl Acad Sci. Aug. 6, 2013; 110(32): pp. 13144-13149.
Brincat SL, Miller EK. Frequency-specific hippocampal-prefrontal interactions during associative learning. Nat Neurosci. Apr. 2015; 18(4): pp. 576-581.
McNamara CG, Tejero-Cantero A, Trouche S, Campo-Urriza N, Dupret D. Dopaminergic neurons promote hippocampal reactivation and spatial memory persistence. Nat Neurosci. 2014 12//print; 17(12): pp. 1658-1660.
Ji D, Wilson MA. Coordinated memory replay in the visual cortex and hippocampus during sleep. Nat Neurosci. 2007; 10(1): pp. 100-107.
Kali S, Dayan P. Off-line replay maintains declarative memories in a model of hippocampal-neocortical interactions. Nat Neurosci. 2004; 7(3): pp. 286-294.
Rolls ET. Hippocampo-cortical and cortico-cortical backprojections. Hippocampus. 2000; 10: pp. 380-388.
Creutzfeldt OD, Fromm GH, Kapp H. Influence of transcortical d-c currents on cortical neuronal activity. Exp Neurol. Jun. 1962; 5: pp. 436-452.
Sederberg PB, Kahana MJ, Howard MW, Donner EJ, Madsen JR. Theta and gamma oscillations during encoding predict subsequent recall. J Neurosci Off J Soc Neurosci. Nov. 26, 2003; 23(34): pp. 10809-10814.
Osipova D, Takashima A, Oostenveld R, Fernandez G, Maris E, Jensen O. Theta and gamma oscillations predict encoding and retrieval of declarative memory. J Neurosci. 2006; 26(28): pp. 7523-7531.
Fröhlich F, McCormick DA. Endogenous electric fields may guide neocortical network activity. Neuron. Jul. 15, 2010; 67(1): pp. 129-143.
Ngo, H. V. V., Martinetz, T., Born, J., & Mölle, M. (2013). Auditory closed-loop stimulation of the sleep slow oscillation enhances memory. Neuron, 78(3), pp. 545-553.
Office Action 1 for U.S. Appl. No. 15/332,787, dated Sep. 18, 2018.
Response to Office Action 1 for U.S. Appl. No. 15/332,787, dated Nov. 6, 2018.
Notice of Allowance for U.S. Appl. No. 15/332,787, dated Jan. 17, 2019.
Bikson, M., Bestmann, S., & Edwards, D. (2013). Neuroscience: transcranial devices are not playthings. Nature, 501(7466), pp. 167-167.
Brunoni, A. R., Nitsche, M. A., Bolognini, N., Bikson, M., Wagner, T., Merabet, L., . . . & Ferrucci, R. (2012). Clinical research with transcranial direct current stimulation (tDCS): challenges and future directions. Brain stimulation, 5(3), pp. 175-195.
Choe, J., Coffman, B. A., Bergstedt, D. T., Ziegler, M. D., & Phillips, M. E. (2016). Transcranial direct current stimulatior modu-

(56) References Cited

OTHER PUBLICATIONS lates neuronal activity and learning in pilot training. Frontiers in human neuroscience, 10, pp. 1-25.
Schultz DM, Webster L, Kosek P, et al. Sensor-driven position-adaptive spinal cord stimulation for chronic pain. Pain Physician 2012;15: pp. 1-12.
Jacobson, L., Koslowsky, M., & Lavidor, M. (2012). tDCS polarity effects in motor and cognitive domains: a meta-analytical review. Experimental brain research, 216(1), pp. 1-10.
Osorio I, Frei MG, Sunderam S, et al. Automated seizure abatement in humans using electrical stimulation. Ann Neurol 2005;57: pp. 258-268.
Berényi, A., Belluscio, M., Mao, D., & Buzsáki, G. (2012). Closed-loop control of epilepsy by transcranial electrical stimulation. Science, 337(6095), pp. 735-737.
Tergau, F., Naumann, U., Paulus, W., & Steinhoff, B. J. (1999). Low-frequency repetitive transcranial magnetic stimulation improves intractable epilepsy. The Lancet, 353(9171), p. 2209.
Nitsche, M. A., Cohen, L. G., Wassermann, E. M., Priori, A., Lang, N., Antal, A., . . . & Pascual-Leone, A. (2008). Transcranial direct current stimulation: state of the art 2008. Brain stimulation, 1(3), pp. 206-223.
Ferrucci, R., Mameli, F., Guidi, I., Mrakic-Sposta, S., Vergari, M., Marceglia, S. E. E. A., . . . & Priori, A. (2008). Transcranial direct current stimulation improves recognition memory in Alzheimer disease. Neurology, 71(7), pp. 493-498.
Clark, V. P., Coffman, B. A., Mayer, A. R., Weisend, M. P., Lane, T. D., Calhoun, V. D., . . . & Wassermann, E. M. (2012). TDCS guided using fMRI significantly accelerates learning to identify concealed objects. Neuroimage, 59(1), pp. 117-128.
Gálvez-García, G., Albayay, J., Rehbein, L., & Tornay, F. (2017). Mitigating Simulator Adaptation Syndrome by means of tactile stimulation. Applied Ergonomics, 58, pp. 13-17.
Ngo, H. V. V., Miedema, A., Faude, I., Martinetz, T., Mölle, M., & Born, J. (2015). Driving Sleep Slow Oscillations by Auditory Closed-Loop Stimulation—A Self-Limiting Process. The Journal of Neuroscience, 35(17), pp. 6630-6638.
Cox, R., Korjoukov, I., de Boer, M., & Talamini, L. M. (2014). Sound asleep: processing and retention of slow oscillation phase-targeted stimuli. PloS one, 9(7), e101567, pp. 1-12.
Santostasi, G., Malkani, R., Riedner, B., Bellesi, M., Tononi, G., Paller, K. A., & Zee, P. C. (2016). Phase-locked loop for precisely timed acoustic stimulation during sleep. Journal of neuroscience methods, 259, pp. 101-114.
Van Elmpt WJ, Nijsen TM, Griep PA, et al. A model of heart rate changes to detect seizures in severe epilepsy. Seizure 2006;15: pp. 366-375.
Schade CM, Schultz DM, Tamayo N, et al. Automatic adaptation of neurostimulation therapy in response to changes in patient position: results of the Posture Responsive Spinal Cord Stimulation (PRS) Research Study. Pain Physician 2011;14: pp. 407-417.
Little S, Pogosyan A, Neal S, et al. Adaptive deep brain stimulation in advanced Parkinson disease. Ann Neurol 2013;74: pp. 449-457.
Office Action 1 for U.S. Appl. No. 15/947,733, dated Feb. 1, 2019.
Notification of Transmittal of International Search Report and the Written Opinion of the International Searching Authority for PCT/US2018/026614; dated Aug. 27, 2018.
International Search Report of the International Searching Authority for PCT/US2018/026614; dated Aug. 27, 2018.
Written Opinion of the International Searching Authority for PCT/US2018/026614; dated Aug. 27, 2018.

Krause, B., & Cohen Kadosh, R. (2014). Not all brains are created equal: the relevance of individual differences in responsiveness to transcranial electrical stimulation. Frontiers in systems neuroscience, vol. 8, article 25, pp. 1-12.
Santarnecchi, E., Muller, T., Rossi, S., Sarkar, A., Polizzotto, N. R., Rossi, A., & Kadosh, R. C. (2016). Individual differences and specificity of prefrontal gamma frequency-tACS on fluid intelligence capabilities. Cortex, 75, pp. 33-43.
Bikson, M., Bestmann, S., & Edwards, D. (2013). Neuroscience: transcranial devices are not playthings. Nature, 501(7466), p. 167.
Schultz DM, Webster L, Kosek P, et al. (2012). Sensor-driven position-adaptive spinal cord stimulation for chronic pain. Pain Physician,15: pp. 1-12.
Philip P, Demotes-Mainard J, Bourgeois M, Vincent JD. (1991). Efficiency of transcranial electrostimulation on anxiety and insomnia symptoms during a washout period in depressed patients a double-blind study. Biol Psychiatry. Mar. 1;29(5): pp. 451-456.
Weiss MF. (1973). The treatment of insomnia through the use of electrosleep: an EEG study. J Nerv Ment Dis. Aug.; 157(2): pp. 108-120.
Lande RG, Gragnani C. (2013) Efficacy of cranial electric stimulation for the treatment of insomnia: a randomized pilot study. Complement Ther Med.;21(1): pp. 8-13. doi: 10.1016/j.ctim.2012.11.007.
Crenshaw MC, Edinger JD. (1999). Slow-Wave Sleep and Waking Cognitive Performance Among Older Adults With and Without Insomnia Complaints Physiology & Behavior, vol. 66, Issue 3, pp. 485-492.
Tyler WJ, Boasso AM, Mortimore HM, et al. (2015) Transdermal neuromodulation of noradrenergic activity suppresses psychophysiological and biochemical stress responses in humans. Scientific Reports;5:13865, pp. 1-17. doi:10.1038/srep13865.
Landolt, HP, Dijk, DJ, Achermann, P, Borbély, AA. (1996). Brain Research, 738(2): pp. 205-212.
Caffarel, J, Gibson, GJ, Harrison, JP, Griffiths, CJ, Drinnan, MJ. (2006). Comparison of manual sleep staging with automated neural network-based analysis in clinical practice. Med Biol Eng Comput., 44(1-2): pp. 105-110.
Santostasi, G et al. (2016). Phase-locked loop for precisely timed acoustic stimulation during sleep. J Neurosci Methods, 259: pp. 101-114.
Nordin, M., Akerstedt, T. & Nordin, S. "Psychometric evaluation and normative data for the Karolinska Sleep Questionnaire," Sleep Biol. Rhythms, Oct. 2013, vol. 11, Issue 4, pp. 216-226.
Li, et al. (2009). Unscented Kalman filter for brain-machine interfaces. Public Library of Science, 4(7): e6243, pp. 1-18.
Dmochowski JP, Datta A, Bikson M, Su Y, Parra LC. Optimized multi-electrode stimulation increases focality and intensity at target. J Neural Eng. 8(4):046011, pp. 1-16, 2011.
Weigenand, A., Mölle, M., Werner, F., Martinetz, T., & Marshall, L. (2016). Timing matters: openloop stimulation does not improve overnight consolidation of word pairs in humans. European Journal of Neuroscience, 44(6), pp. 2357-2368.
Hoy, K. E., Emonson, M. R., Arnold, S. L., Thomson, R. H., Daskalakis, Z. J., & Fitzgerald, P. B. (2013). Testing the limits: investigating the effect of tDCS dose on working memory enhancement in healthy controls. Neuropsychologia, 51(9), pp. 1777-1784.
Notice of Allowance for U.S. Appl. No. 15/338,118, dated Mar. 11, 2019.
Response to Office Action 1 for U.S. Appl. No. 15/947,733, dated Apr. 16, 2019.
Notice of Allowance for U.S. Appl. No. 15/947,733, dated May 8, 2019.

* cited by examiner

TARGETED STEERABLE TRANSCRANIAL INTERVENTION TO ACCELERATE MEMORY CONSOLIDATION

CROSS-REFERENCE TO RELATED APPLICATIONS

The present application is a Continuation-in-Part application of U.S. application Ser. No. 15/332,787, filed on Oct. 24, 2016, now patented as U.S. Pat. No. 10,307,592, which was filed as a non-provisional application of U.S. Provisional Application No. 62/245,730, filed on Oct. 23, 2015, the entirety of which are hereby incorporated by reference.

The present application is ALSO a Continuation-in-Part application of U.S. application Ser. No. 15/227,922, Aug. 3, 2016, now patented as U.S. Pat. No. 10,092,753, which was filed as a non-provisional application of U.S. Provisional Patent Application No. 62/210,907 filed Aug. 27, 2015, entitled, "Method to Enhance Specific Memories with tCS During Slow-Wave Sleep," AND of which is a non-provisional of U.S. Provisional Patent Application No. 62/210,890 filed Aug. 27, 2015, entitled, "Transcranial Intervention to Weaken Traumatic Memories," the entirety of which are incorporated herein by reference.

The present application is ALSO a Continuation-in-Part application of U.S. application Ser. No. 15/947,733, filed on Apr. 6, 2018, now patented as U.S. Pat. No. 10,413,724, which was filed as a non-provisional application of U.S. Provisional Application No. 62/516,350, filed on Jun. 7, 2017, the entirety of which are hereby incorporated by reference. U.S. application Ser. No. 15/947,733 is a Continuation-in-Part patent application of U.S. application Ser. No. 15/332,787, filed in the United States on Oct. 24, 2016, entitled, "Method and System to Accelerate Consolidation of Specific Memories Using Transcranial Stimulation," which is a Non-Provisional patent application of U.S. Provisional Application No. 62/245,730, filed in the United States on Oct. 23, 2015, entitled, "Method and System to Accelerate Consolidation of Specific Memories Using Transcranial Stimulation," the entirety of which are hereby incorporated by reference. U.S. application Ser. No. 15/947,733 is ALSO a Continuation-in-Part patent application of U.S. application Ser. No. 15/583,983, filed in the United States on May 1, 2017, entitled, "System and Method for Neurostimulation-Enhanced Second Language Acquisition," which is a Non-Provisional patent application of U.S. Provisional Application No. 62/330,440, filed in the United States on May 2, 2016, entitled, "A Method for Neurostimulation-Enhanced Second Language Acquisition," the entirety of which are hereby incorporated by reference.

The present application is ALSO a non-provisional patent application of U.S. Provisional Application No. 62/570,669, filed on Oct. 11, 2017, the entirety of which is hereby incorporated by reference.

The present application is ALSO a non-provisional patent application of U.S. 62/558,133 filed on Sep. 13, 2017, the entirety of which is hereby incorporated by reference.

The present application is ALSO a non-provisional patent application of U.S. 62/537,892, filed on Jul. 27, 2017, the entirety of which is hereby incorporated by reference.

GOVERNMENT RIGHTS

This invention was made with government support under U.S. Government Contract Number W911NF-16-C-0018, DARPA RAM Replay. The government has certain rights in the invention.

BACKGROUND OF INVENTION

(1) Field of Invention

The present invention relates to a brain stimulation system and, more specifically, to a system for targeted and steerable transcranial intervention to accelerate memory consolidation.

(2) Description of Related Art

In operational tasks (as in many business and educational scenarios), it can be critically important to quickly integrate and accurately recall based on limited exposure to information. To assist this need, some prior art stimulation systems have been developed to promote memory consolidation. Such stimulation systems are based on the well-supported idea that when people sleep, the memory system "replays" memories, which means they are recalled from short term hippocampal memory and conveyed to the slower-learning cortical structures, where they are slowly integrated nondestructively into the long-term memory store. Although any memory in the hippocampus has a chance of being replayed during sleep, there is a greater probability that a specific memory will be replayed if it was recently learned and related to some emotional content or high immediate reward. Unfortunately, many things people need to learn are boring or tedious, and the reward for learning them may be a long way off.

One prior art technique applies a unique high-definition transcranial current stimulation (HD-tCS) montage, a SpatioTemporal Amplitude-Modulated Pattern (STAMP) of currents including endogenous rhythms across the scalp during a distinct experience or skill learning to "tag" it by becoming associated with it in the short-term memory. The same STAMP tag is then applied later offline during quiet waking or slow-wave sleep (specifically during cortical UP states) to cue the specific memory with which it was associated to be replayed, thereby consolidated in long-term memory. The STAMP method has the advantage that it will not degrade task-performance or distract attention from learning the task, unlike other methods that employ audio or olfactory associations with a memory to tag it and later cue its replay. Unfortunately, the STAMP method can require that many (e.g., at least 64) and possibly up to 256 electrodes must be applied to the subject's scalp in order to make possible a wide variety of unique STAMP patterns. Each electrode must make good contact with the scalp, so they are applied one at a time and tested to ensure the electrical properties match every other electrode (see Literature Reference No. 2 in the List of Incorporated Literature References for a description of procedures for applying such electrodes). The process is long and tedious, usually requiring a specialist who can test and adjust each electrode. Further, electrodes have a limited life, so it is advisable to maintain a log of use and replace older electrodes. Additionally, high-density electrodes must be applied with gel, which is messy; sponge electrodes that can be applied by non-specialists on themselves have a larger footprint and cannot be closely spaced. If this memory consolidation method can be made easy to apply, it could be used regularly by businessmen in meetings, soldiers on patrol or in training, or students in daily classes. But to transition this technology to a product that would be widely accepted and adopted even outside a clinical setting for wider home use by non-specialists, it is critical to reduce the number of electrodes to less than a half-dozen, which will exponentially decrease the time and trouble. Another drawback to the prior art is that to create the same STAMP pattern when the specific memory is learned, and then to recreate that some pattern each succeeding night for consolidation during sleep, all of the voluminous electrodes must be applied in exactly the same locations, and with exactly the same electrical conductivity properties.

Thus, a continuing need exists for a transcranial stimulation system that only requires a desirably small number of electrodes (e.g., as few as four) during waking task acquisition and during operation to create the tag or STAMP to be associated with the memory, which is a localized and steerable 3D region of stimulation possibly deep below the surface of the cortex.

SUMMARY OF INVENTION

This disclosure provides a system for steerable transcranial intervention to accelerate memory consolidation. In various embodiments, the system includes one or more processors and a memory. The memory is a non-transitory computer-readable medium having executable instructions encoded thereon, such that upon execution of the instructions, the one or more processors perform several operations, such as generating a unique transcranial and steerable stimulation tag to associate with memory of a task or event; and activating at least a plurality of electrodes to apply the unique transcranial stimulation tag during the occurrence of the event or task to be consolidated.

In another aspect, the unique transcranial and steerable stimulation tag is a targeted, localized, transcranially applied pattern of electrical stimulation in a three-dimensional region of the brain using at least four electrodes during the occurrence of the event or task to be consolidated.

In yet another aspect, a unique transcranial and steerable stimulation tag is generated for each memory to be consolidated.

In yet another aspect, the unique transcranial and steerable stimulation tag that is activated during the occurrence of the event or task to be consolidated is activated during a positive phase of a subject's slow wave oscillations during non-REM sleep to stimulate replay of the memory and promote its consolidation to long-term memory.

In another aspect, each unique transcranial stimulation tag is generated as a function of variations of a stimulation pattern that include its three-dimensional start location, frequency, intensity, and a temporal trajectory through a subject's brain that varies frequency, intensity, and location as a function of time.

In another aspect, a duration of the task or event to be consolidated is estimated in advance, and the generated unique transcranial and steerable stimulation tag is clipped if the actual task or event is shorter than estimated, or repeated if the actual task or event is longer than estimated.

In yet another aspect, a rate of the trajectory of the unique transcranial and steerable stimulation tag can be increased by a factor of at least ten times during sleep application to increase efficacy of induced memory reactivation, as sleep replays are known to be temporally compressed relative to waking brain dynamics.

In another aspect, activating the plurality of electrodes includes activating at least four electrodes to apply the unique transcranial and steerable stimulation tag, and in doing so, the region of stimulation is varied during application of the electrical stimulation.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
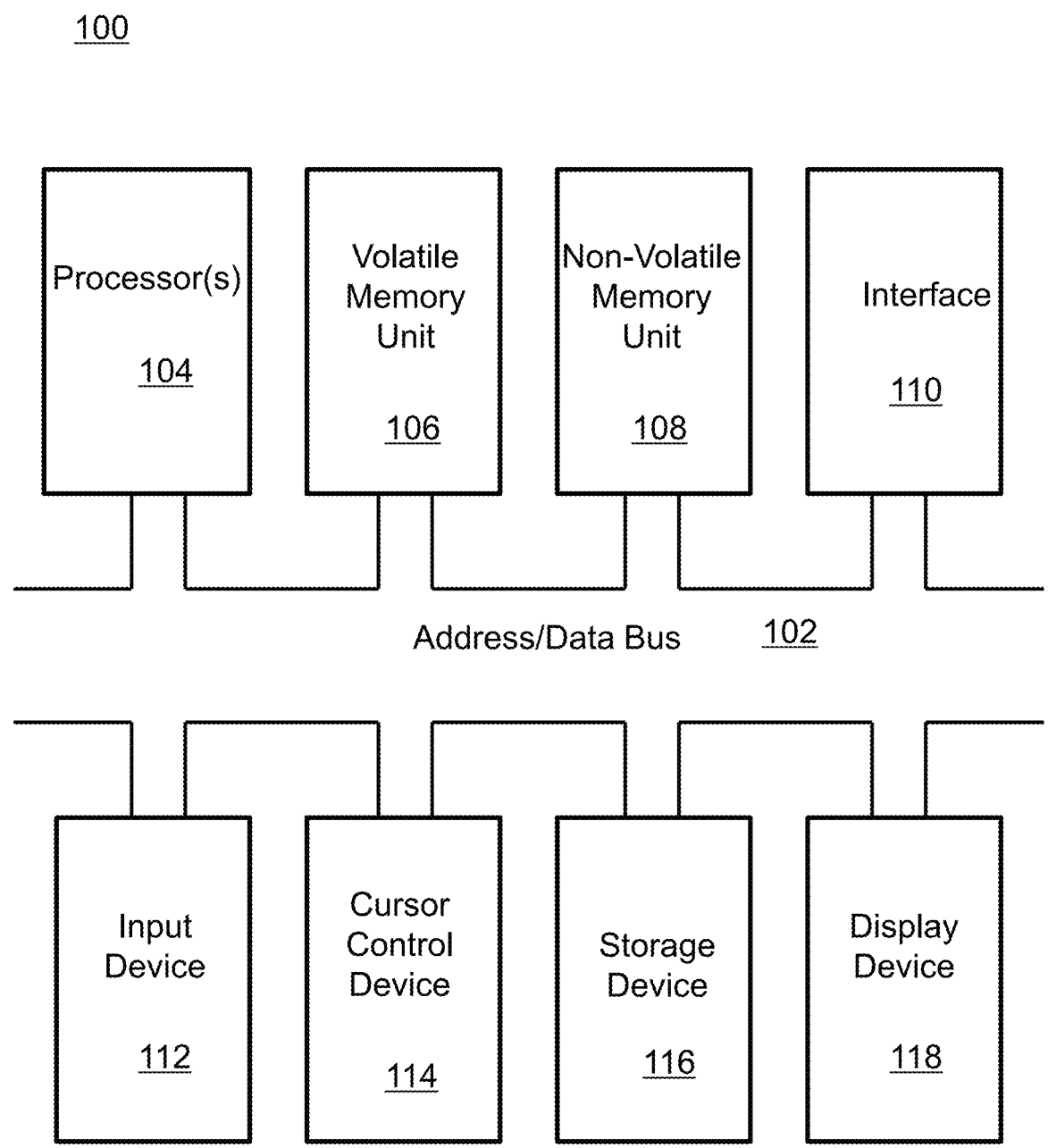
FIG. 1 is a block diagram depicting the components of a system according to various embodiments of the present invention.

The present invention relates to a brain stimulation system and, more specifically, to a system for targeted and steerable transcranial intervention to accelerate memory consolidation. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of incorporated literature references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) List of Incorporated Literature References

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Nir Grossman, David Bono, Nina Dedic, Suhasa B. Kodandaramaiah, Andrii Rudenko, Ho-Jun Suk, Antonino M. Cassara, Esra Neufeld, Niels Kuster, Li-Huei Tsai, Alvaro Pascual-Leone, Edward S. Boyden (2017). Noninvasive Deep Brain Stimulation via Temporally Interfering Electric Fields. Cell 169, 1029-1041 Jun. 1, 2017.
2. Woods et al. (2016). A technical guide to tDCS, and related non-invasive brain stimulation tools. Clinical Neurophysiology, 127:1031-1048.
3. Santostasi, Giovanni, et al. "Phase-locked loop for precisely timed acoustic stimulation during sleep." *Journal of neuroscience methods* 259 (2016): 101-114.
4. Liu, Hechen, and Markus Schneider. "Similarity measurement of moving object trajectories." Proceedings of the third ACM SIGSPATIAL international workshop on geostreaming. ACM, 2012. https://www.cise.ufl.edu/~mschneid/Research/papers/LS12IWGS.pdf (2) Principal Aspects Various embodiments of the invention include three "principal" aspects. The first is a system for transcranial stimulation. The system is typically in the form of a computer system operating software or in the form of a "hard-coded" instruction set, and can include all of the electrodes and/or sensors as may be required per this disclosure. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
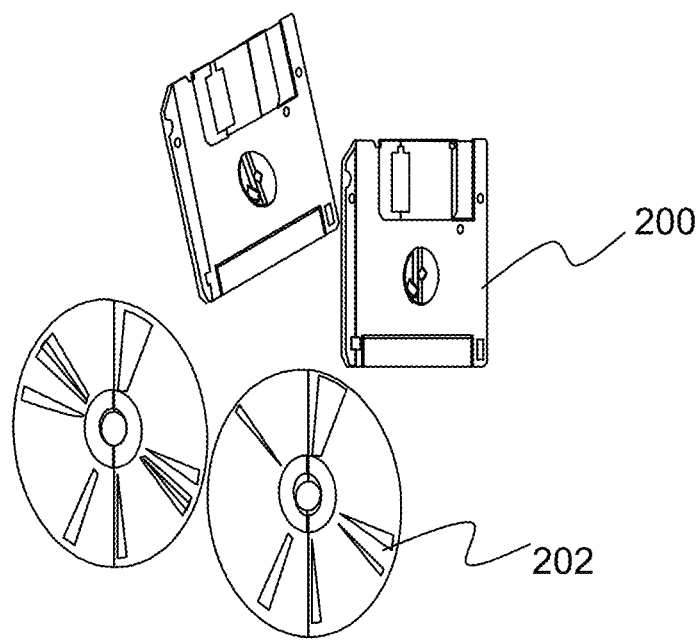
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

This disclosure provides a system and method to accelerate memory consolidation by applying a targeted, localized, transcranially applied pattern of electrical stimulation in a specific protocol. As opposed to the prior art, which described applying a weak, broadly-distributed "high-density" pattern of transcranial stimulation across the scalp with a voluminous number of electrodes (e.g., at least 64 but up to 256), the system of the present disclosure applies a focal area of stimulation with as few as four electrodes, creating a highly-localized region of stimulation that can potentially be located deep below the cortex, and can be moved over time, changing the intensity and size of the stimulated spot. It should be noted that although as few as four electrodes are described as being sufficient, the invention is not intended to be limited thereto as it merely requires a minimum number of electrodes where the pattern of stimulation is created by an interference pattern between multiple electrodes, each emitting AC current at a possibly different frequency, where the current cycles constructively or destructively interact. Thus, although a system employing four electrodes is described and has been proven to work (see Literature Reference No. 1), the system can also be implemented with, for example, three electrodes where triangulation is used to triangulate on a region.

In operational tasks (as in many business and educational scenarios), it can be critically important to quickly integrate and accurately recall based on limited exposure to information. A purpose of this invention is to promote memory consolidation to make this possible. It is based on the well-supported idea that when people sleep, the memory system "replays" memories, which means they are recalled from short term hippocampal memory and conveyed to the slower-learning cortical structures, where they are slowly integrated nondestructively into the long-term memory store. Although any memory in hippocampus has a chance of being replayed during sleep, there is a greater probability that a specific memory will be replayed if it was recently learned and related to some emotional content or high immediate reward.

A prior art technique (U.S. application Ser. No. 15/227,922 (the '922 application), filed Aug. 3, 2016, incorporated herein by reference) applies a unique HD-tCS montage, a SpatioTemporal Amplitude-Modulated Pattern (STAMP) of currents including endogenous rhythms across the scalp during a distinct experience or skill learning to "tag" it by becoming associated with it in the short-term memory. The same STAMP tag is then applied later offline during quiet waking or slow-wave sleep (specifically during cortical UP states) to cue the specific memory with which it was associated to be replayed, thereby consolidated in long-term memory. The STAMP method has the advantage that it will not degrade task-performance or distract attention from learning the task, unlike other methods that employ audio or olfactory associations with a memory to tag it and later cue its replay. Unfortunately, the prior art technique requires a lot of electrodes (e.g., between 64 and 256 electrodes) that must be applied to the subject's scalp in order to make possible a wide variety of unique STAMP patterns.

The system and method of the present disclosure improves upon the prior art (as taught in the '922 application) by dramatically reducing the required number of electrodes to exponentially decrease the time and trouble in setting up and implementing the system. The reduced number of electrodes (e.g., such as only four) also make the item much more portable for mobile and in field applications. Another advantage of the system of the present disclosure is that this new reduced electrode (e.g., four) technique does not have rigid constraints on electrode placement (as was the case with prior art devices), since the region of stimulation can be steered. This means that if the location of stimulation when it is first applied is computed, that location can be recreated at a later time regardless of where the few (e.g., four) electrodes are placed on the scalp. It also improves over the prior art on targeting a focal region of the brain using as few as four electrodes, in that the intervention of the present system moves the location of the movable stimulation region during a certain time, as well as temporally varying its intensity. The intervention can be spatially controlled to focus on, or avoid, the most task relevant regions of the brain. That is, if a task is of a type that has been found to strongly activate brain region A, one skilled in the art could design a pattern of stimulation to focus on brain regions other than A, in order to avoid interfering with normal operation of the brain region A. Thus, the system described herein not only targets a specific static location, but can be used to move targeted location during the temporal duration of an event to be remembered, and to also change the intensity and size of the stimulation spot during the same time, thereby associating the moving stimulation pattern with the memory, and then using that same pattern again during slow-wave sleep in order to cue recall of the memory, promoting its consolidation.

The system and method can be implemented in a product that provides a targeted and personalized closed-loop system for enhancing memory in both normal subjects and those with learning difficulties related to memory consolidation. The interventions employing closed-loop high-density electroencephalography (HD-EEG) sensing and Focal-tACS (transcranial alternating current stimulation) stimulation can be incorporated into existing stimulation systems, such as those produced by Neuroelectrics, Soterix Medical, and/or EGI. Neurolectrics is located at 210 Broadway, Suite 201, Cambridge 02139, Mass., USA. Soterix Medical is located at 237 W 35th St, New York, N.Y. 10001, while EGI (or Electrical Geodesics, Inc.) is located at 500 East 4th Ave., Suite 200, Eugene, Oreg. 97401. An integrated brain monitoring and transcranial stimulation system will have broad applicability in research and rehabilitation, for both commercial and military applications.

Products resulting from this work allow people to reinforce episodic memories and acquire skills faster as they sleep. As an added benefit, if the stimulation is applied in an oscillatory manner at the same frequency and phase as the slow wave oscillations during sleep (as disclosed in U.S. Provisional Application No. 62/570,669, which is incorporated herein by reference), the intervention will increase overall cognitive alertness by promoting longer periods of slow-wave-sleep (SWS) (or deep sleep). For many reasons and as can be appreciated by those skilled in the art, the system of this disclosure provides several advantages. The augmentation technology and therapeutic procedure is safe and non-invasive; it does not require drugs or surgery. The system can be trained on an event that is identified by the subject either before the event happens, or some time after it happens (in which case the user turns on the system as the event is recalled as clearly as possible). Further, the therapy is targeted at specific memories, while other memories are unaffected. Specific details are provided below.

(4) Specific Details of Various Embodiments

Figure 3:
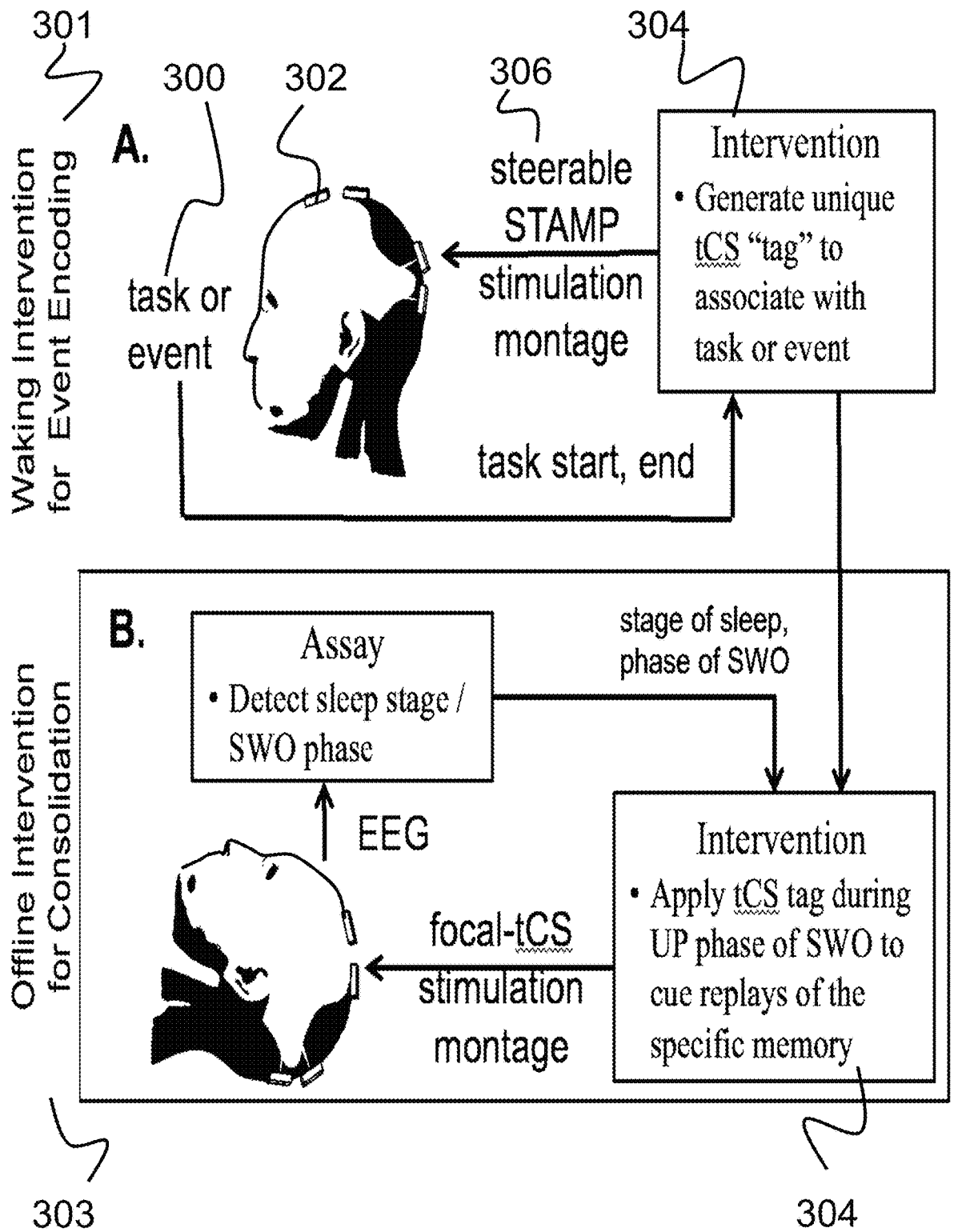
FIG. 3 is an illustration of the two phases of operation, wake and sleep.

The system and method described in this disclosure is designed to improve consolidation of specific memories (referred to herein as an "event"). For further understanding, FIG. 3 provides an illustration of the two phases of operation of the system, the waking intervention for event encoding phase 301 and the offline intervention for consolidation phase 303. A desired implementation is that when the event 300 is first experienced (e.g., when the user is learning something new), he/she wears an intervention system comprising of at least four steerable STAMP stimulating electrodes 302 (more electrodes can be employed to produce more than one simultaneous steerable spot of stimulation for more complex patterns). Steerable STAMP employs the recent prior art temporal interference method (see Literature Reference No. 1, or any other suitable technique), which can target the stimulation region of a transcranially applied alternating current stimulation (tACS) intervention without physically moving electrodes, by altering the respective frequencies of the AC current delivered to a fixed set of electrodes. In other words, the stimulated region is steered by altering the frequency and magnitude of currents delivered to the fixed set of electrodes 302.

Using this capability, a highly targeted and localized brain region that can be deep within the brain can be stimulated by an electrical intervention. The Intervention module 304 generates a unique steerable STAMP montage 306 that the brain will associate with the task or event as it encodes it through selective activation of the electrodes 302. There is an infinite number of patterns possible by varying the temporal-spatial trajectory of the region of stimulation (via the electrodes 302), the temporally changing size of the region as it moves, and the power of stimulation over this time.

The steerable STAMP montage 306 is generated to become associated with an event to be remembered, and subsequently used during slow-wave sleep to cue recall of the memory of the event, thereby promoting consolidation of the memory. The point of moving the area of stimulation is to provide another dimension for creating a unique stimulation cue to associate with a memory, and also to allow that unique cue to focus on, or avoid, certain task-related brain regions (ones that are highly activated during the memory to be consolidated).

Figure 4:
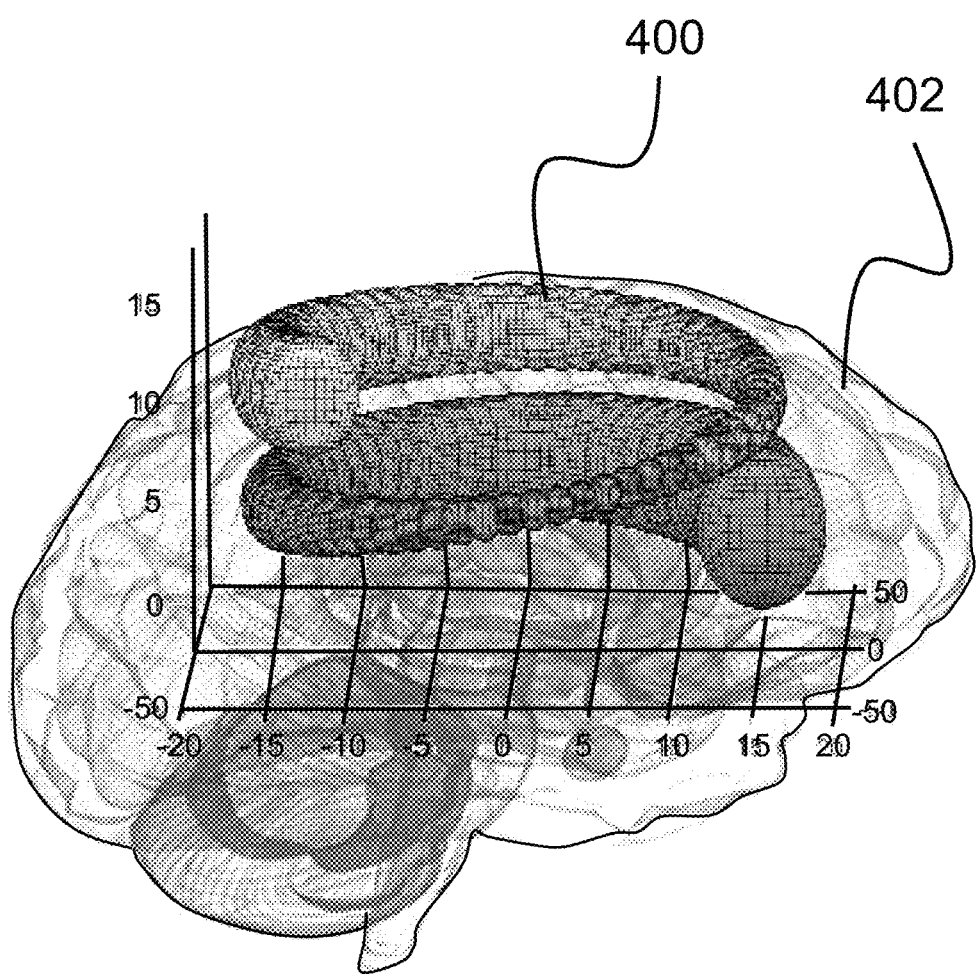
FIG. 4 is an illustration of a steerable STAMP pattern.

For example, FIG. 4 provides an illustration depicting an extreme example, where the stimulation spot 400 is moved rapidly in a spiral pattern around the brain 402, varying in size as it moves. This is the steerable STAMP tag, and it should be unique relative to any other tags used for different memories being learned. In this non-limiting example, the spherical region of stimulation moves in a spiral trajectory through the brain volume, changing size over time according to a determined unique pattern, which is the basic idea of a steerable pattern of simulation.

Figure 5:
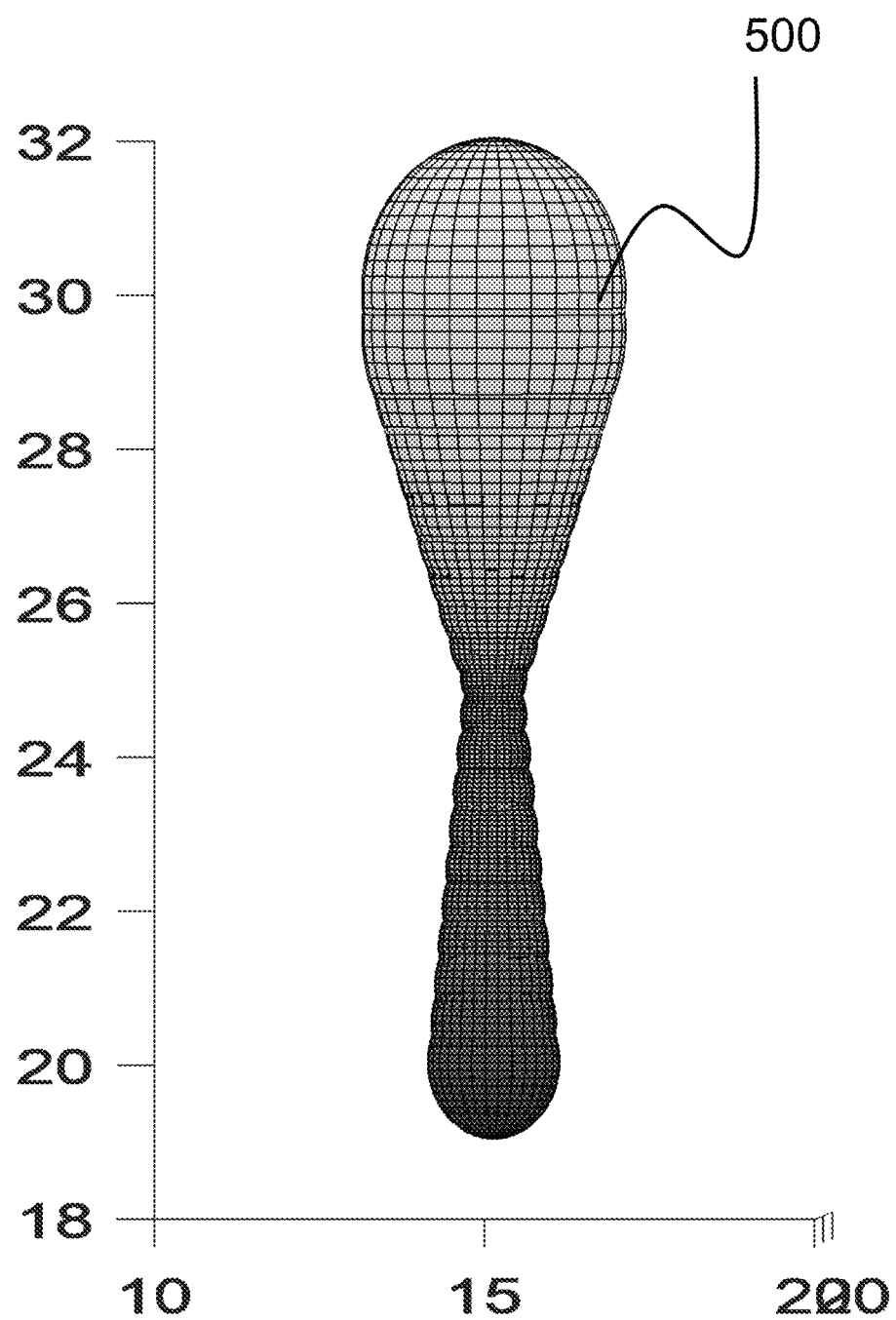
FIG. 5 is an example illustration of a pattern that moves the sphere of stimulation upward or downward in a linear motion, but changing the size of the stimulation region and possibly other parameters.
Figure 6:
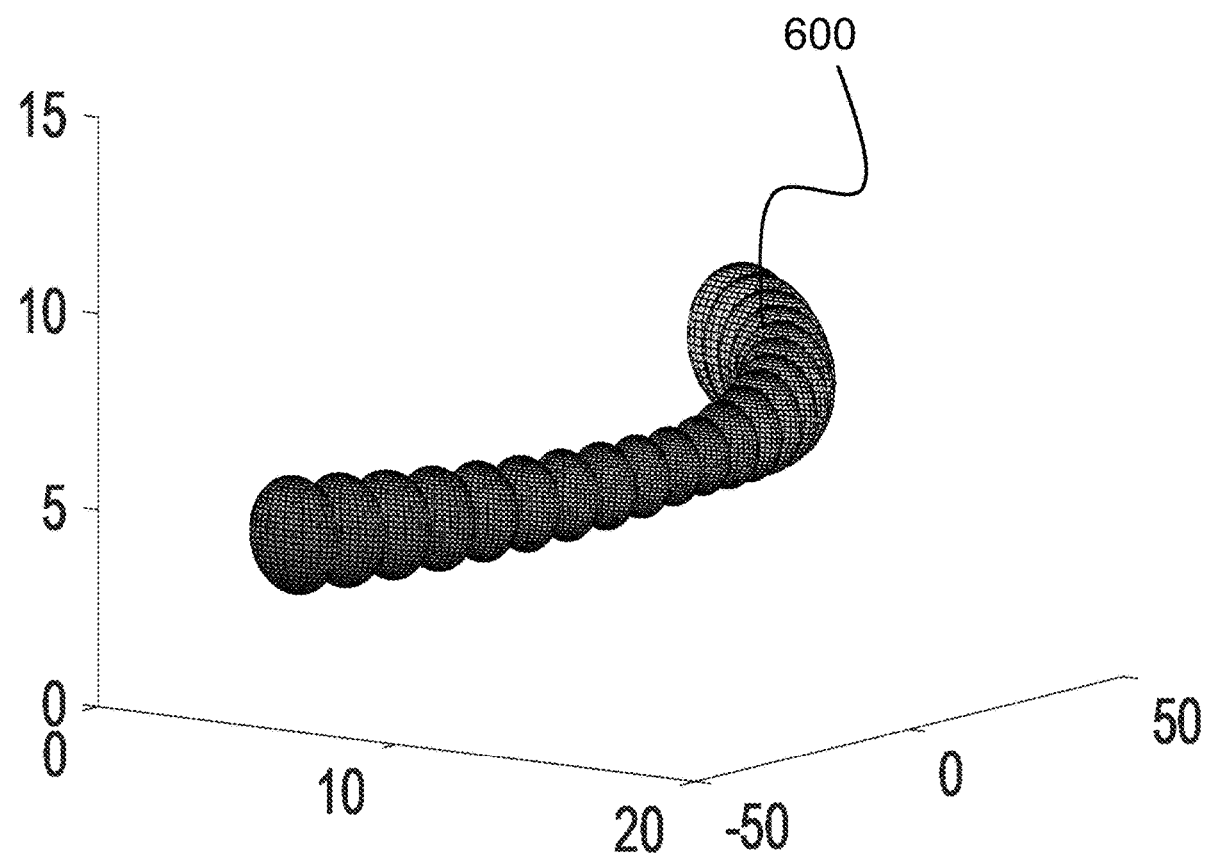
FIG. 6 is an example illustration of the steerable STAMP pattern that moves the sphere of stimulation in a nonlinear trajectory that might be used across the prefrontal region of the brain.

Some other examples of steerable STAMP tags are in depicted in FIGS. 5 and 6. FIG. 5 is an example illustration of a pattern 500 that moves the sphere of stimulation upward or downward in a linear motion, but changes the size of the stimulation region and possibly other parameters. FIG. 6 is an example illustration of the steerable STAMP pattern 600 that moves the sphere of stimulation in a nonlinear trajectory that might be directed across brain region such as the prefrontal region (e.g., across the cortical region behind the forehead).

Once an event is tagged in this way, the tag used must be stored for use later during sleep to cue consolidation of the memory. Later, during sleep or quiet waking (i.e., during the offline intervention for consolidation phase 303), the user again wears the intervention system, but this time with an EEG array. The Intervention system 304 monitors the EEG data to detect the stage of sleep, and applies the same steerable STAMP tag to cue the memory during transcranially sensed positive ("UP") phases of slow-wave sleep (SWS) to stimulate, and the montage becomes a cue that promotes replays (a kind of recall) of the memory, thereby accelerating its consolidation into long-term memory.

U.S. application Ser. No. 15/947,733 (which is incorporated herein by reference) disclosed a method for sensing the UP phases of the slow-wave oscillation (SWO) and applying transcranial stimulation in closed-loop. A similar technique can be used to apply the steerable STAMP. The sleep intervention can be applied each night until the memory is consolidated. The level of consolidation of a memory is judged as a function of task performance or recall of the event in the days or weeks after it is encoded.

A unique tag must be generated for each memory that is to be consolidated. As mentioned above, a tag is a localized region of tACS stimulation, and it is generated by a unique temporal trajectory through the brain that varies intensity, speed, spatial extent, and location as a function of time. The duration must be limited to the anticipated length of the task or event to be consolidated (e.g., based on, for example, historical data of the subject or others performing such a task or event). If the duration cannot be anticipated ahead of time, a tag can be generated for an estimated duration and either clipped if the task is shorter than the estimate, or repeated if the task goes longer than estimated. It would be possible to reverse the trajectory multiple times if an event is extended in duration. The speed of movement is another parameter that may be changed. In either case, the tag used in sleep to consolidate the memory must be equal to whatever clipped or extended tag was used during waking. When the tag is used during sleep, it is applied in the UP phases, which each only last 400 ms to 1 second long. It is likely that the waking event that was tagged lasts longer than that so there are two approaches: (1) speed up the application of the tag so it takes less than 1 second to apply it, or (2) apply the tag at the speed it was applied during waking, possibly extending over more than UP phase. Either alternative is acceptable, and depending on the type of event being learned, one or the other may achieve better results. However, during sleep, memory replays are often speeded up by a factor of 10 or more, so it may be preferable to increase the rate at which the stimulation region is steered across a trajectory through the brain by a factor of 10 or more during the offline intervention for consolidation phase 303.

When associating the steerable STAMP with a memory to be consolidated, it can be applied either during the actual event to be remembered or during viewing of the event from a body camera replay of the event, so the user can learn unanticipated events after they occur. If a camera view of the event is not available, the user can still sit quietly after the event and recall it in as much detail as possible while the system tags the episode. The system needs to ascertain if a steerable STAMP trajectory that is generated on the fly to tag a new event is unique enough given the library of previously used steerable STAMP trajectories. Uniqueness may be judged by maximizing a distance metric as a function of all the parameters of the steerable STAMP; e.g. (temporal trajectory, temporal intensity, temporal spatial extent), and these factors can be weighted. The preferred weighting is [3, 1, 2] times the function parameters mentioned. Distance between trajectories or two vectors is a well-known procedure. For example, Literature Reference No. 4 describes how to compare two trajectories. This invention can be combined with sensory cueing (such as auditory or olfactory-based targeted memory reactivation) as well as other forms of cueing with electromagnetic and mechanical stimulation. For example, a particular sound can be combined with the steerable STAMP, or a tactile pattern on an area of skill such as a forearm or the tongue. This invention can be combined with closed-loop auditory stimulation during sleep (see Literature Reference No. 3) to boost slow oscillations in order to provide more windows of opportunity to apply steerable STAMPs. The application of steerable STAMPs during sleep can be optimized and scheduled based on behavioral predictions of a personalized memory model to prioritize cueing for weaker memories.

(5) Control of a Device

Figure 7:
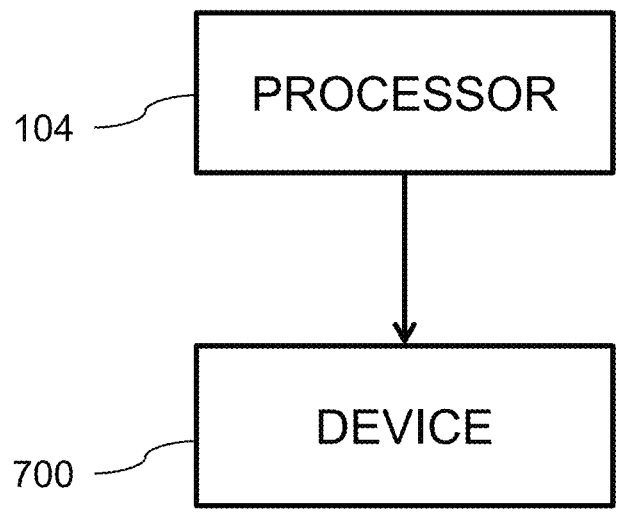
FIG. 7 is a block diagram depicting control of a device according to various embodiments.

As shown in FIG. 7, a processor 104 may be used to control a device(s) 700 (e.g., an electrode array of a plurality of electrodes (e.g., four or more electrodes positioned on the scalp of a subject)) based on determining when to apply the steerable STAMP montage or a focal transcranial stimulation montage. The device 500 is any suitable device that can used to provide a steerable focal transcranially applied pattern of stimulation to a subject, non-limiting examples of which include an array of electrical stimulation electrodes (e.g., the electrodes depicted as element 302 in FIG. 3, and/or including high resolution arrays in a headcap or individually applied to a subject), a magnetic field, or ultrasound. Thus, in this example, the processor 104 activates the device(s) 700 (array of electrodes (e.g., element 302 in FIG. 3)) based on the process described herein to provide a transcranial stimulation to the subject. The device 700 can also be items that provide sensory cueing (such as alerts for auditory or olfactory-based targeted memory reactivation) as well as other forms of cueing with electromagnetic and mechanical stimulation.

Figure 8:
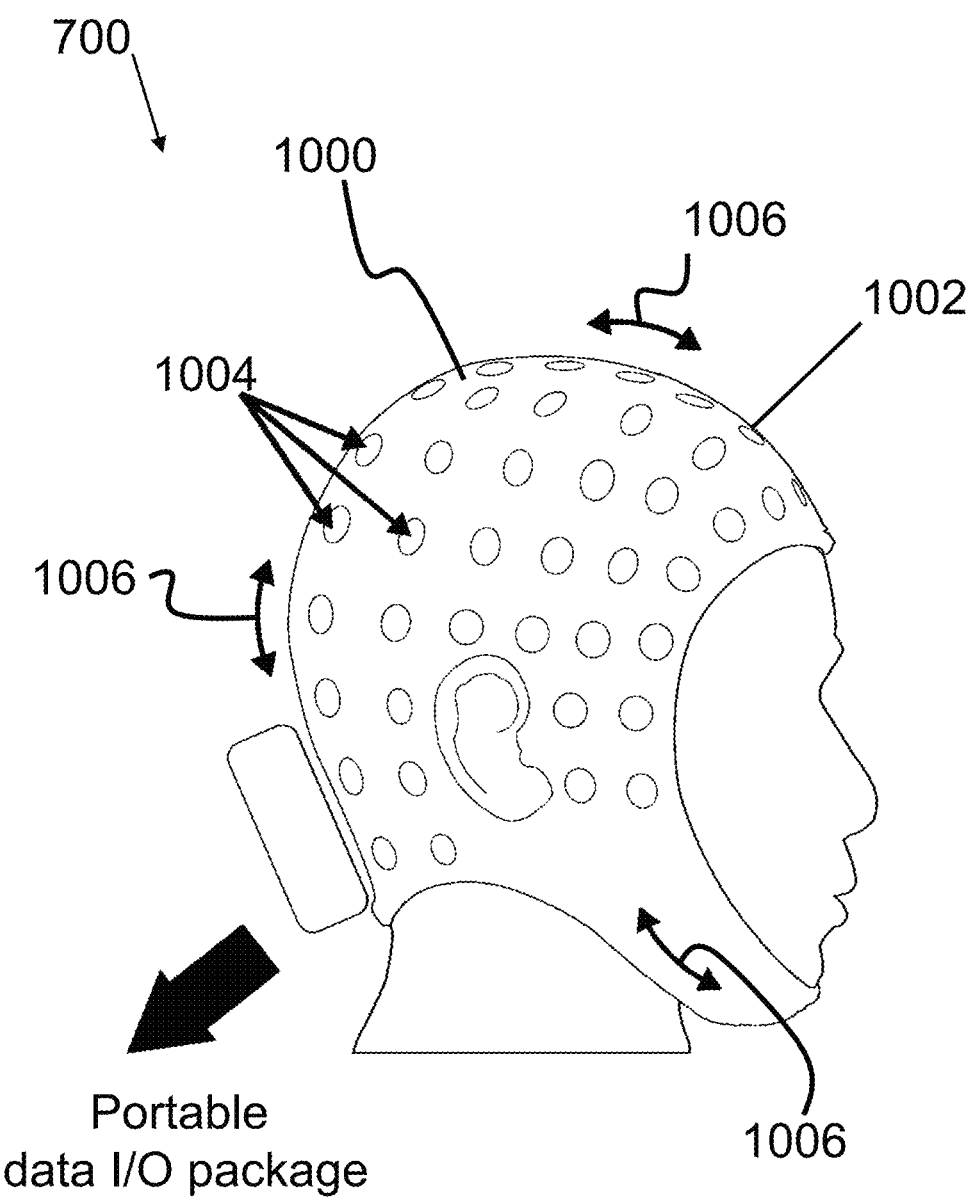
FIG. 8 is an illustration of a headcap according to various embodiments of the present invention.

Although not limited thereto, FIG. 8 provides another example of the device 700 in which the device 700 is a headcap 1000 containing one or both of: 1) sensors 1002 to detect high-resolution spatiotemporal neurophysiological activity (e.g., EEG data); and 2) a montage of stimulation elements 1004 (i.e., electrodes) that can be used to direct current flow to specific cortical subregions per the process as described herein. While the electrodes are shown as individually applied to the subject in FIG. 3, FIG. 8 depicts another aspect in which the electrodes are incorporated into a headcap 1000. It should be understood that additional headgear configurations can also be implemented so long as they include the sensors and/or stimulation elements, additional non-limiting examples include a non-elastic headcap, nets (such as hair or head nets), bands, visors, helmets, or other headgear, etc.

In some embodiments, the headcap 1000 is formed of an elastic material containing sensing components that record neurophysiological activity via electrical potentials on the scalp (electroencephalogram (EEG)) and backscattered near infrared light detecting cortical bloodflow (functional near-infrared spectroscopy, FNIRS). In some embodiments, both sensors are desirably present in the cap in order to delineate cortical activity at high spatial and temporal resolution, and the headcap is elastic (compression fitting 1006) to fixate the sensitive recording elements to ensure the procurement of clean, artifact-free signals to feed the system (and to provide for sensor and stimulator consistency). Stimulation elements 1004 are also present in the same headcap 1000 device, which includes multiple sets of surface electrodes (e.g., as few as four) which are precisely controlled to direct currents through the scalp per the process described above. In some embodiments, these stimulation elements 1004 maintain consistent electrical environments—particularly impedance values—in order to provide appropriate stimulation throughout cognitive enhancement. The control software (i.e., the system as described herein) of the electrodes also enables the modification of the injected electrical current, as varying stimulation protocols can be leveraged to achieve differential effects to neurological tissue. In the same vein, the headcap 1000 itself in some embodiments is configurable—that is, the headcap 1000 is constructed such that all sensing and recording components have modular configurability to allow recordings to be taken from diverse areas of the scalp, and stimulation to be applied to a wide array of brain structures. For example, the headcap 1000 is depicted as having a plurality of configurable harness locations for receiving a sensor 1002 and/or stimulator 1004. The sensors 1002 and stimulators 1004 can be formed and combined in a single harness for attaching at a harness location or they can be separately attached. The sensors 1002 and stimulators 1004 may also be spring-loaded to maintain sufficient contact with the wearer's skin. For various embodiments, one, some, or all of these components are present in the headcap 1000, and these characteristics of the device are helpful for the application of transcranial stimulation for cognitive enhancement.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for steerable transcranial intervention to accelerate memory consolidation, the system comprising:
   one or more processors and a memory, the memory being a non-transitory computer-readable medium having executable instructions encoded thereon, such that upon execution of the instructions, the one or more processors perform operations of:
      generating a unique transcranial and steerable stimulation tag to associate with memory of a task or event;
      activating at least a plurality of electrodes to apply the unique transcranial and steerable stimulation tag during an occurrence of the task or event; and
      wherein activating the plurality of electrodes includes applying an electrical stimulation to a region of stimulation through the unique transcranial and steerable stimulation tag such that the region of stimulation is varied during application of unique transcranial and steerable stimulation tag.

2. The system as set forth in claim 1, wherein the unique transcranial and steerable stimulation tag is a targeted, localized, transcranially applied pattern of electrical stimulation in a three-dimensional region of a brain using at least four electrodes from the plurality of electrodes during the occurrence of the task or event.

3. The system as set forth in claim 1, wherein the unique transcranial and steerable stimulation tag that is activated during the occurrence of the task or event is activated during a positive phase of a subject's slow wave oscillations during non-REM sleep.

4. The system as set forth in claim 1, wherein the unique transcranial and steerable stimulation tag is generated as a function of variations of a stimulation pattern that include its three-dimensional start location, frequency, intensity, and a temporal trajectory through a subject's brain that varies frequency, intensity, and location as a function of time.

5. The system as set forth in claim 1, wherein an estimated duration of the task or event is estimated in advance, and the generated unique transcranial and steerable stimulation tag is clipped if an actual duration of the task or event is shorter than the estimated duration, or repeated if the actual duration of the task or event is longer than the estimated duration.

6. The system as set forth in claim 1, wherein a rate at which a trajectory of the unique transcranial and steerable stimulation tag is traversed through a brain can be increased by a factor of at least ten times during sleep application.

7. The system as set forth in claim 1, wherein activating the plurality of electrodes includes activating at least four electrodes to apply electrical stimulation through the unique transcranial and steerable stimulation tag, and in doing so, a region of stimulation is varied during application of the electrical stimulation.

8. A computer program product for steerable transcranial intervention to accelerate memory consolidation, the computer program product comprising:
   a non-transitory computer-readable medium having executable instructions encoded thereon, such that upon execution of the instructions by one or more processors, the one or more processors perform operations of:
      generating a unique transcranial and steerable stimulation tag to associate with memory of a task or event;
      activating at least a plurality of electrodes to apply the unique transcranial and steerable stimulation tag during an occurrence of the task or event; and
      wherein activating the plurality of electrodes includes applying an electrical stimulation to a region of stimulation through the unique transcranial and steerable stimulation tag such that the region of stimulation is varied during application of unique transcranial and steerable stimulation tag.

9. The computer program product as set forth in claim 8, wherein the unique transcranial and steerable stimulation tag is a targeted, localized, transcranially applied pattern of electrical stimulation in a three-dimensional region of a brain using at least four electrodes from the plurality of electrodes during the occurrence of the task or event.

10. The computer program product as set forth in claim 8, wherein the unique transcranial and steerable stimulation tag that is activated during the occurrence of the task or event is activated during a positive phase of a subject's slow wave oscillations during non-REM sleep.

11. The computer program product as set forth in claim 8, wherein the unique transcranial and steerable stimulation tag is generated as a function of variations of a stimulation pattern that include its three-dimensional start location, frequency, intensity, and a temporal trajectory through a subject's brain that varies frequency, intensity, and location as a function of time.

12. The computer program product as set forth in claim 8, wherein an estimated duration of the task or event is estimated in advance, and the generated unique transcranial and steerable stimulation tag is clipped if an actual duration of the task or event is shorter than the estimated duration, or repeated if the actual duration of the task or event is longer than the estimated duration.

13. The computer program product as set forth in claim 8, wherein a rate at which a trajectory of the unique transcranial and steerable stimulation tag is traversed through a brain can be increased by a factor of at least ten times during sleep application.

14. The computer program product as set forth in claim 8, wherein activating the plurality of electrodes includes activating at least four electrodes to apply electrical stimulation through the unique transcranial and steerable stimulation tag, and in doing so, a region of stimulation is varied during application of the electrical stimulation.

15. A computer implemented method for steerable transcranial intervention to accelerate memory consolidation, the method comprising an act of:
   causing one or more processors to execute instructions encoded on a non-transitory computer-readable medium, such that upon execution, the one or more processors perform operations of:
      generating a unique transcranial and steerable stimulation tag associate with memory of a task or event;
      activating at least a plurality of electrodes to apply the unique transcranial and steerable stimulation tag during an occurrence of the task or event; and
      wherein activating the plurality of electrodes includes applying an electrical stimulation to a region of stimulation through the unique transcranial and steerable stimulation tag such that the region of stimulation is varied during application of unique transcranial and steerable stimulation tag.

16. The method as set forth in claim 15, wherein the unique transcranial and steerable stimulation tag is a targeted, localized, transcranially applied pattern of electrical stimulation in a three-dimensional region of a brain using at least four electrodes from the plurality of electrodes during the occurrence of the task or event.

17. The method as set forth in claim 15, wherein the unique transcranial and steerable stimulation tag that is activated during the occurrence of the task or event is activated during a positive phase of a subject's slow wave oscillations during non-REM sleep.

18. The method as set forth in claim 15, wherein the unique transcranial and steerable stimulation tag is generated as a function of variations of a stimulation pattern that include its three-dimensional start location, frequency, intensity, and a temporal trajectory through a subject's brain that varies frequency, intensity, and location as a function of time.

19. The method as set forth in claim 15, wherein an estimated duration of the task or event is estimated in advance, and the generated unique transcranial and steerable stimulation tag is clipped if an actual duration of the task or event is shorter than the estimated duration, or repeated if the actual duration of the task or event is longer than the estimated duration.

20. The method as set forth in claim 15, wherein a rate at which a trajectory of the unique transcranial and steerable stimulation tag is traversed through a brain can be increased by a factor of at least ten times during sleep application.

21. The method as set forth in claim 15, wherein activating the plurality of electrodes includes activating at least four electrodes to apply electrical stimulation through the unique transcranial and steerable stimulation tag, and in doing so, a region of stimulation is varied during application of the electrical stimulation.

* * * * *